(12) United States Patent
Lin et al.

(10) Patent No.: US 6,911,190 B2
(45) Date of Patent: Jun. 28, 2005

(54) PROCESS AND APPARATUS FOR TREATING CONTAMINATED GAS

(75) Inventors: Shu-Sung Lin, Hsinchuang (TW); Ching-Chih Lai, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 10/745,717

(22) Filed: Dec. 24, 2003

(65) Prior Publication Data

US 2004/0156767 A1 Aug. 12, 2004

Related U.S. Application Data

(63) Continuation of application No. 10/012,749, filed on Dec. 7, 2001, now abandoned.

(30) Foreign Application Priority Data

Apr. 12, 2001 (TW) .......................... 90108832 A

(51) Int. Cl.[7] .............................................. C07C 11/24
(52) U.S. Cl. .................................. 423/245.1; 588/205
(58) Field of Search ................................ 588/205, 206, 588/218, 221, 242, 246; 423/245.1, 239.1, 244.09, 244.1, 244.11; 502/324, 337, 338

(56) References Cited

U.S. PATENT DOCUMENTS

| | | |
|---|---|---|
| 4,844,874 A | 7/1989 | de Vries |
| 5,063,030 A | 11/1991 | Sweetman |
| 5,145,657 A | 9/1992 | Kobayashi et al. |
| 5,414,201 A | 5/1995 | Greene |
| 5,460,792 A | 10/1995 | Rosenbaum |
| 5,472,516 A | 12/1995 | Hanson et al. |
| 5,492,676 A | 2/1996 | Katatani et al. |
| 5,547,648 A | 8/1996 | Buchanan et al. |
| 5,977,427 A | 11/1999 | Tamata et al. |
| 6,106,853 A | 8/2000 | Cox et al. |

FOREIGN PATENT DOCUMENTS

| | | |
|---|---|---|
| JP | 56-44025 A1 | 4/1981 |
| JP | 62-221422 A1 | 9/1987 |
| JP | 8-173517 A1 | 7/1996 |

*Primary Examiner*—Stanley S. Silverman
*Assistant Examiner*—Edward M. Johnson
(74) *Attorney, Agent, or Firm*—Darby & Darby

(57) ABSTRACT

The present invention provides a process and apparatus for treating contaminated gas. A contaminated gas containing volatile organic compounds is continuously introduced into a reactor to allow the gas to contact a metal oxide catalyst and an oxidant for a period of time. The concentration of the volatile organic compounds can be thus reduced. The treated gas is then continuously emitted from the reactor. The concentration of the organic compounds of the emitted gas and/or the concentration of the oxidant are continuously monitored, and the oxidant feeding amount is controlled according to the monitored concentration. By means of the process of the present invention, volatile organic compound-containing waste gas with high humidity can be effectively treated, and the utility rate of the oxidant can be increased.

11 Claims, 1 Drawing Sheet

PROCESS AND APPARATUS FOR TREATING CONTAMINATED GAS

CROSS-REFERENCE TO RELATED APPLICATION

This application claims priority from Taiwanese Patent Application No. 90108832, filed Apr. 12, 2001 and is a continuation of U.S. application Ser. No. 10/012,749, filed Dec. 7, 2001. Each of the aforementioned applications is hereby incorporated herein by reference in its entirety.

BACKGROUND OF THE INVENTION

1. Field of the Invention

The present invention relates to a process for treating contaminated gas, and more particularly to a catalytic oxidation process involving control of the oxidant feeding amount by means of continuous monitoring of the organic compound concentration and oxidant concentration in the emitted gas.

2. Description of the Prior Art

Presently, environmental issues are a major concern in the manufacturing industries. Waste gas containing volatile organic compounds (VOC) must be treated according to government regulations. Treatment technology for waste gas can be generally classified into three types: incineration, adsorption by activated carbon, and advanced catalytic oxidation at ambient temperature. Incineration requires high heat levels. Adsorption by activated carbon requires frequent changing of the carbon, resulting in large amounts of waste. High level catalytic oxidation process requires a temperature higher than 200° C.

U.S. Pat. No. 5,755,977 discloses a catalytic oxidation process at ambient temperature (20° C.–30° C.). Contaminated air containing VOC is treated by an oxidant such as ozone or hydrogen peroxide and an iron oxide catalyst. However, the treatment efficiency is relatively low with waste gas with high humidity (higher than 20%). The removal ratio of waste gas containing trichloroethylene (TCE) is lower than 30%. Moreover, the utility rate of the oxidant is low; thus, excess oxidant is emitted. Since ozone is generally used as an oxidant and considered as a toxic compound, its toxicity causes air pollution.

SUMMARY OF THE INVENTION

An object of the present invention is to solve the above-mentioned problems and provide a process for treating contaminated gas. By means of this process, contaminated gas containing volatile organic compounds with high humidity is treated with enhanced efficiency. Moreover, the utility rate of the oxidant is increased; thus, the emitted oxidant amount is decreased, preventing compounded pollution.

To achieve the above objects, the first process for treating a contaminated gas includes continuously introducing a contaminated gas containing volatile organic compounds into a reactor, allowing the contaminated gas into the reactor to contact a metal oxide catalyst and an oxidant for a period of time to reduce the concentration of the volatile organic compounds, continuously expelling the treated gas from the reactor, continuously monitoring a value selected from the concentration of the organic compounds of the emitted gas, the concentration of the oxidant of the emitted gas, and a combination thereof, and controlling the oxidant feeding amount according to the monitoring value.

The second process for treating a contaminated gas of the present invention includes continuously introducing a contaminated gas containing volatile organic compounds into a reactor, allowing the contaminated gas into the reactor to contact a metal oxide catalyst and an oxidant for a period of time to reduce the concentration of the volatile organic compounds, and continuously emitting the treated gas from the reactor.

The contaminated gas to be introduced has a humidity between 20% and 100% and a temperature of T° C., and the contaminated gas is heated to a temperature between $(T+5)°$ C. and $(T+70)°$ C. in the treating step.

The present invention can also treat a contaminated gas containing ozone. Thus, the third process for treating a contaminated gas of the present invention includes continuously introducing a contaminated gas containing ozone into a reactor, allowing the contaminated gas into the reactor to contact a metal oxide catalyst for a period of time to reduce the concentration of ozone, and continuously emitting the treated gas from the reactor.

The contaminated gas to be introduced has a humidity between 20% and 100% and a temperature of T° C., and the contaminated gas is heated to a temperature between $(T+5)°$ C. and $(T+70)°$ C. in the treating step.

The present invention also provides an apparatus for treating a contaminated gas, which includes an oxidant generator for generating an oxidant, a reactor for accommodating a metal oxide catalyst, a continuously introduced contaminated gas containing volatile organic compounds, and the oxidant generated from the oxidant reactor, such that the concentration of the volatile organic compounds in the contaminated gas is decreased and the treated gas is continuously emitted from the reactor.

The apparatus also includes a monitoring device for continuously monitoring a value of the emitted gas and a controlling device for controlling the oxidant feeding amount according to the monitoring value. The value to be monitored is selected from the concentration of the organic compounds of the emitting gas, the concentration of the oxidant of the emitting gas, and a combination thereof.

DETAILED DESCRIPTION OF THE INVENTION

Figure 1:
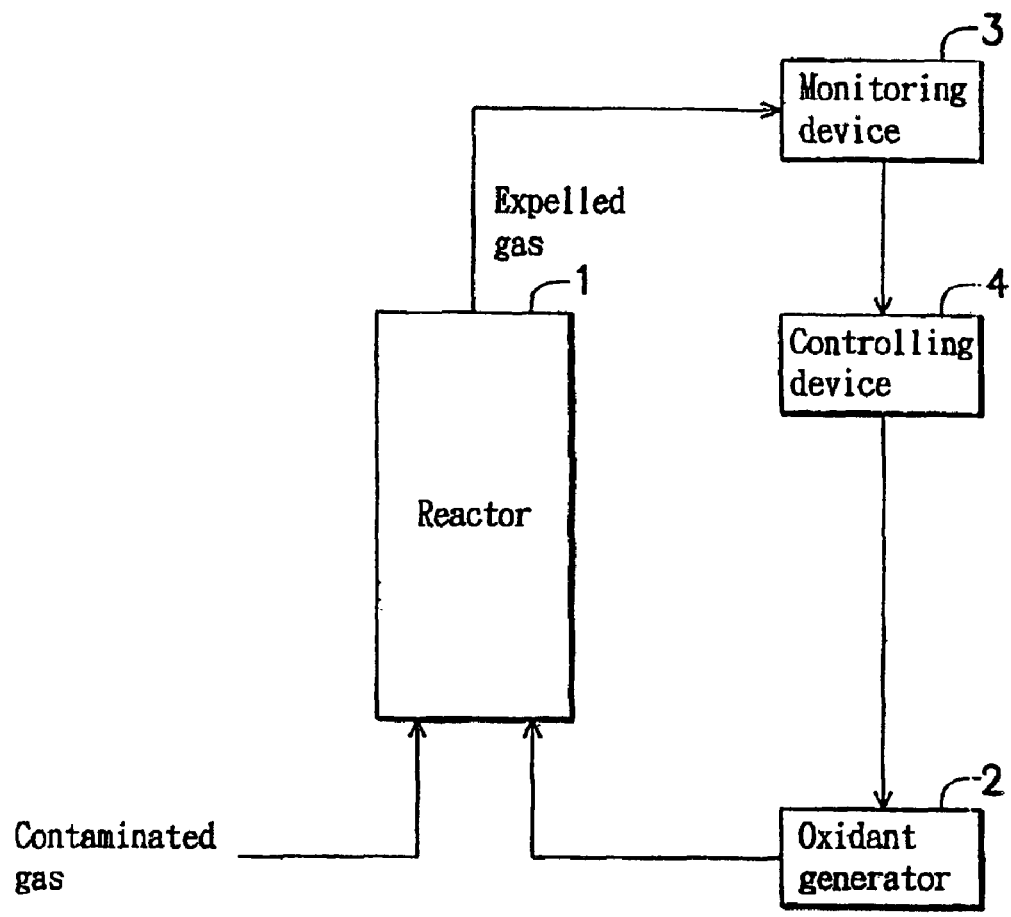
FIG. 1 shows a schematic diagram of the an apparatus for treating contaminated gas according to the present invention.

The present invention uses two methods to treat high humidity waste gas and reduce the emitted oxidant's amount. One method involves continuously monitoring the organic compound concentration in the emitted gas, the oxidant concentration in the emitted gas, or both the organic compound concentration and the oxidant concentration. The oxidant feeding amount is then controlled according to the monitored value. The other method involves controlling the treatment temperature according to the humidity of waste gas.

Specifically, the method to control the oxidant feeding amount is explained below. When the concentration of the organic compounds of the emitted gas is monitored, the control method increases the oxidant feeding amount when the organic compound concentration monitored is higher than the preceding concentration monitored. When the organic compound concentration monitored is lower than the preceding concentration monitored, the oxidant feeding amount is decreased. When the concentration of the oxidant of the emitted gas is monitored, the control method decreases the oxidant feeding amount when the oxidant concentration monitored is higher than the preceding concentration monitored. Thus, the oxidant feeding amount is kept from creeping too high. Therefore, the utility rate of oxidant is increased, thus decreasing the emitted oxidant amount.

In the present invention, the volatile organic compound in the contaminated gas can be chlorinated alkanes, chlorinated alkenes, alkanes, alkenes, aromatic compounds, ketones, ethers, alcohols, organic acids, amines, or mixtures thereof. The contaminated gas can also include an ill-smelling material, which can be nitrogen-containing compound, sulfur-containing compound, or mixtures thereof.

The metal oxide catalyst suitable for use in the present invention can be iron oxide, manganese oxide, or nickel oxide. Suitable oxidant can be hydrogen peroxide ($H_2O_2$), ozone ($O_3$), or a mixture thereof.

The process of the present invention is particularly effective with contaminated gas with high humidity, for example, with a humidity higher than 10%, preferably with a humidity of 20% to 100%.

As to control of the treatment temperature according to the humidity of waste gas, the temperature of the contaminated gas is increased in the treating step by 5° C. to 70° C.

A preferred embodiment of the present invention is explained in FIG. 1, where gas containing organic contaminants and/or ill-smelling material is passed through a pretreatment device (not shown) to filter out particles, which are then introduced to a reactor 1. Simultaneously, oxidant is provided by an oxidant generator 2 and continuously introduced into the reactor 1. The reactor 1 is filled with a catalyst bed, and the catalyst is a metal oxide. Thus, the oxidant and the contaminated gas to be treated are mixed into the reactor and contact the metal oxide. The organic contaminants' amounts are thereby reduced by a catalytic oxidation process in the reactor 1.

A monitoring device 3 is provided at the downstream of the emitted gas from the reactor 1. The monitoring device 3 continuously monitors the organic compound concentration and oxidant concentration in the emitted gas. The signal of the monitored concentration is then transmitted to a controlling device 4. The controlling device 4 then controls the oxidant feeding amount from the oxidant generator 2 according to the monitored concentration. When the organic compound concentration monitored is higher than the preceding concentration monitored, the oxidant feeding amount is increased. When the organic compound concentration monitored is lower than the preceding concentration monitored, the oxidant feeding amount is decreased. When the oxidant concentration monitored is higher than the preceding concentration monitored, the oxidant feeding amount is decreased.

The following examples are intended to illustrate the process and the advantages of the present invention more fully without limiting its scope, since numerous modifications and variations will be apparent to those skilled in the art.

TREATMENT OF WASTE GAS CONTAINING TCE

COMPARATIVE EXAMPLES 1–3

Conventional High Level Catalytic Oxidation Process at Ambient Temperature

The waste gas to be treated in these examples contained trichloroethylene (TCE). TCE is a representative VOC difficult to biodegrade and with low water solubility. The relative humidity of the waste gas was 5%, 40%, and 80% respectively.

The reactor was filled with a catalyst and ozone was introduced into the reactor. The catalyst used was needle shaped iron oxide (FeOOH). The feeding ozone concentration was 200 ppm.

The waste gas was introduced into the reactor for treatment. The feeding waste gas concentration was maintained at about 100 ppm. The treatment temperature was 25° C.

When steady conditions were achieved, the TCE removal efficiency and $O_3$ utility rate were determined. The retention time was 0.5 seconds. The results are shown in Table 1.

COMPARATIVE EXAMPLE 4

The same procedures as described in Comparative Example 2 were employed except that the ozone feeding amount was doubled (400 ppm). The results are shown in Table 1.

EXAMPLE 1

The same procedures as described in Comparative Example 1 were employed except that ozone was continuously introduced into the reactor and the waste gas treatment device was replaced with the apparatus of the present invention. In the apparatus of the present invention, a monitoring device and a controlling device were provided, such that the organic compound concentration and ozone concentration of the emitted gas was continuously monitored, and the ozone feeding amount was controlled.

When steady conditions were achieved, the TCE removal efficiency and $O_3$ utility rate were determined. The retention time was 0.5 seconds. The results are shown in Table 1.

EXAMPLE 2

The same procedures as described in Example 1 were employed, except that the waste gas used had a relative humidity of 40% and the treatment temperature was raised to 60° C. The results are shown in Table 1.

EXAMPLE 3

The same procedures as described in Example 1 were employed, except that the waste gas used had a relative humidity of 80% and the treatment temperature was raised to 80° C. The results are shown in Table 1.

TABLE 1

|  | Relative humidity of waste gas | Treatment temp. | TCE removal efficiency | $O_3$ utility rate |
|---|---|---|---|---|
| Comparative Example 1 | 5% | 25° C. | 92% | 98% |
| Comparative Example 2 | 40% | 25° C. | 32% | 75% |
| Comparative Example 3 | 80% | 25° C. | 12% | 40% |
| Comparative Example 4* | 40% | 25° C. | 35% | 75% |
| Example 1 | 5% | 25° C. | 93% | 98% |
| Example 2 | 40% | 60° C. | 93% | 98% |
| Example 3 | 80% | 80° C. | 91% | 98% |

*Ozone feeding amount is doubled

From Table 1, it can be seen that for the waste gas with a relative humidity of 5%, the TCE removal efficiency and ozone utility rate are almost the same by means of either the process of the present invention or a conventional high level catalytic oxidation process at ambient temperature.

However, for the waste gas with high humidity (relative humidity=40% and 80%), both the TCE removal efficiency and ozone utility rate by means of the process of the present invention are higher than those by means of a conventional high level catalytic oxidation process at ambient temperature.

TREATMENT OF WASTE GAS CONTAINING OZONE

COMPARATIVE EXAMPLES 5–7

Conventional High Level Catalytic Oxidation Process at Ambient Temperature

The waste gas to be treated in these examples contained 1000 ppm ozone ($O_3$). The relative humidity of the waste gas was 5%, 40%, and 80% respectively.

The reactor was filled with a needle shaped iron oxide (FeOOH) catalyst. The waste gas was introduced into the reactor for treatment. The feeding waste gas concentration was maintained at about 100 ppm. The treatment temperature was 25° C.

When steady conditions were achieved, the $O_3$ treating efficiency was determined. Determination was based on a retention time of 0.5 seconds. The results are shown in Table 2.

EXAMPLE 4

The same procedures as described in Comparative Example 6 were employed, except that the treatment temperature was raised to 60° C. The results are shown in Table 2.

EXAMPLE 5

The same procedures as described in Comparative Example 7 were employed, except that the treatment temperature was raised to 80° C. The results are shown in Table 2.

TABLE 2

|  | Relative humidity of waste gas | Treatment temp. | $O_3$ removal efficiency |
| --- | --- | --- | --- |
| Comparative Example 5 | 5% | 25° C. | 99% |
| Comparative Example 6 | 40% | 25° C. | 75% |
| Comparative Example 7 | 80% | 25° C. | 40% |
| Example 4 | 40% | 60° C. | 99.9% |
| Example 5 | 80% | 80° C. | 99.9% |

From Table 2, it can be seen that for the waste gas with a relative humidity of 40% and 80%, increasing treating temperature greatly enhances the $O_3$ treating efficiency.

The foregoing description of the preferred embodiments of this invention has been presented for purposes of illustration and description. Obvious modifications or variations are possible in light of the above teaching. The embodiments chosen and described provide an excellent illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A process for treating a contaminated gas, comprising the following steps:
   continuously introducing a contaminated gas containing volatile organic compounds into a reactor;
   treating the contaminated gas by allowing the contaminated gas into the reactor to contact a metal oxide catalyst and an oxidant for a period of time to decrease the concentration of the volatile organic compounds;
   continuously emitting the treated gas from the reactor;
   continuously monitoring a value selected from the group consisting of the concentration of the organic compounds of the emitted gas, the concentration of the oxidant of the emitted gas, and a combination thereof; and
   controlling the oxidant feeding amount according to the monitored value,
   wherein the contaminated gas to be introduced has a humidity between 20% and 100% and a temperature of T° C., and the contaminated gas is heated to a temperature between (T+5)° C. and (T+70)° C. in the treating step.

2. The process as claimed in claim 1, wherein
   the monitoring step continuously monitors the concentration of the organic compounds of the emitted gas,
   the controlling step increases the oxidant feeding amount when a second concentration monitored is higher than a first concentration monitored, and decreases the oxidant feeding amount when a second concentration monitored is lower than a first concentration monitored,
   wherein the second concentration is monitored at a time after the first concentration is monitored.

3. The process as claimed in claim 1, wherein
   the monitoring step continuously monitors the concentration of the oxidant of the emitted gas,
   the controlling step decreases the oxidant feeding amount when a second concentration monitored is higher than a first concentration monitored,
   wherein the second concentration is monitored at a time after the first concentration is monitored.

4. The process as claimed in claim 1, wherein the monitoring step continuously monitors both the concentration of the organic compounds of the emitted gas and the concentration of the oxidant of the emitted gas.

5. The process as claimed in claim 1, wherein the volatile organic compound is selected from the group consisting of chlorinated alkanes, chlorinated alkenes, alkanes, alkenes, aromatic compounds, ketones, ethers, alcohols, organic acids, amines, and mixtures thereof.

6. The process as claimed in claim 1, wherein the contaminated gas further contains an ill-smelling material.

7. The process as claimed in claim 6, wherein the ill-smelling material is selected from the group consisting of nitrogen-containing compounds, sulfur-containing compounds, and mixtures thereof.

8. The process as claimed in claim 1, wherein the metal oxide catalyst is selected from the group consisting of iron oxide, manganese oxide, and nickel oxide.

9. The process as claimed in claim 1, wherein the oxidant is selected from the group consisting of hydrogen peroxide ($H_2O_2$), ozone ($O_3$), and a mixture thereof.

10. A process for treating a contaminated gas, comprising the following steps:

continuously introducing a contaminated gas containing volatile organic compounds into a reactor;

treating the contaminated gas by allowing the contaminated gas into the actor to contact a metal oxide catalyst and an oxidant for a period of time to decrease the concentration of the volatile organic compounds; and continuously expelling the treated gas from the reactor;

wherein the contaminated gas to be introduced has a humidity between 20% and 100% and a temperature of T° C., and the contaminated gas is heated to a temperature between (T+5)° C. and (T+70)° C. in the treating step.

11. A process for treating a contaminated gas, comprising the following steps:

continuously introducing a contaminated gas containing ozone into a reactor;

treating the contaminated gas by allowing the contaminated gas into the actor to contact a metal oxide catalyst for a period of time to decrease the concentration of ozone; and continuously expelling the treated gas from the reactor;

wherein the contaminated gas to be introduced has a humidity between 20% and 100% and a temperature of T° C., and the contaminated gas is heated to a temperature between (T+5)° C. and (T+70)° C. in the treating step.

* * * * *